United States Patent [19]

Gebauer

[11] 4,251,455
[45] Feb. 17, 1981

[54] CONTINUOUS CLOSED LOOP NITRATION OF POLYHYDRIC ALCOHOLS

[75] Inventor: Hans-Jürgen Gebauer, Cologne, Fed. Rep. of Germany

[73] Assignee: Josef Meissner GmbH & Co., Cologne, Fed. Rep. of Germany

[21] Appl. No.: 35,754

[22] Filed: May 3, 1979

[30] Foreign Application Priority Data

May 12, 1978 [DE] Fed. Rep. of Germany ....... 2820890

[51] Int. Cl.$^3$ ............................................. C07C 77/02
[52] U.S. Cl. ..................................... 260/467; 260/703
[58] Field of Search ................................ 260/467, 703

[56] References Cited

U.S. PATENT DOCUMENTS

| 2,294,849 | 9/1942 | Olin et al. | 260/467 |
| 3,009,944 | 11/1961 | Brunnberg | 260/467 |
| 3,086,042 | 4/1963 | Blair | 260/467 |
| 3,111,538 | 11/1963 | Stow, Jr. | 260/467 |

FOREIGN PATENT DOCUMENTS

| 832870 | 4/1960 | United Kingdom | 260/467 |
| 837044 | 6/1960 | United Kingdom | 260/467 |

Primary Examiner—Leland A. Sebastian
Attorney, Agent, or Firm—Sprung, Felfe, Horn, Lynch & Kramer

[57] ABSTRACT

A process for the continuous manufacture of a nitric acid ester of a polyhydric alcohol by reacting the polyhydric alcohol with nitrating acid, comprising circulating a stream of waste nitrating acid through a closed loop, injecting nitrosulphuric acid into said circulating stream, cooling the stream downstream of the injection, feeding the alcohol via a mixer into the cooled stream, cooling the stream to remove heat produced by reaction, and separating nitrated polyhydric alcohol from the loop, along with sufficient waste acid to keep the volume in the loop substantially constant, circulation being carried out at a rate such that the average residence time of waste acid in the loop is less than about 15 minutes, preferably about 2 to 5 minutes. This avoids the prolonged storage of large quantities of waste acid which is inherently dangerous. When the system is to be shut down all the circulating waste acid can be replaced by fresh nitrosulphuric acid, relatively small in volume.

5 Claims, 1 Drawing Figure

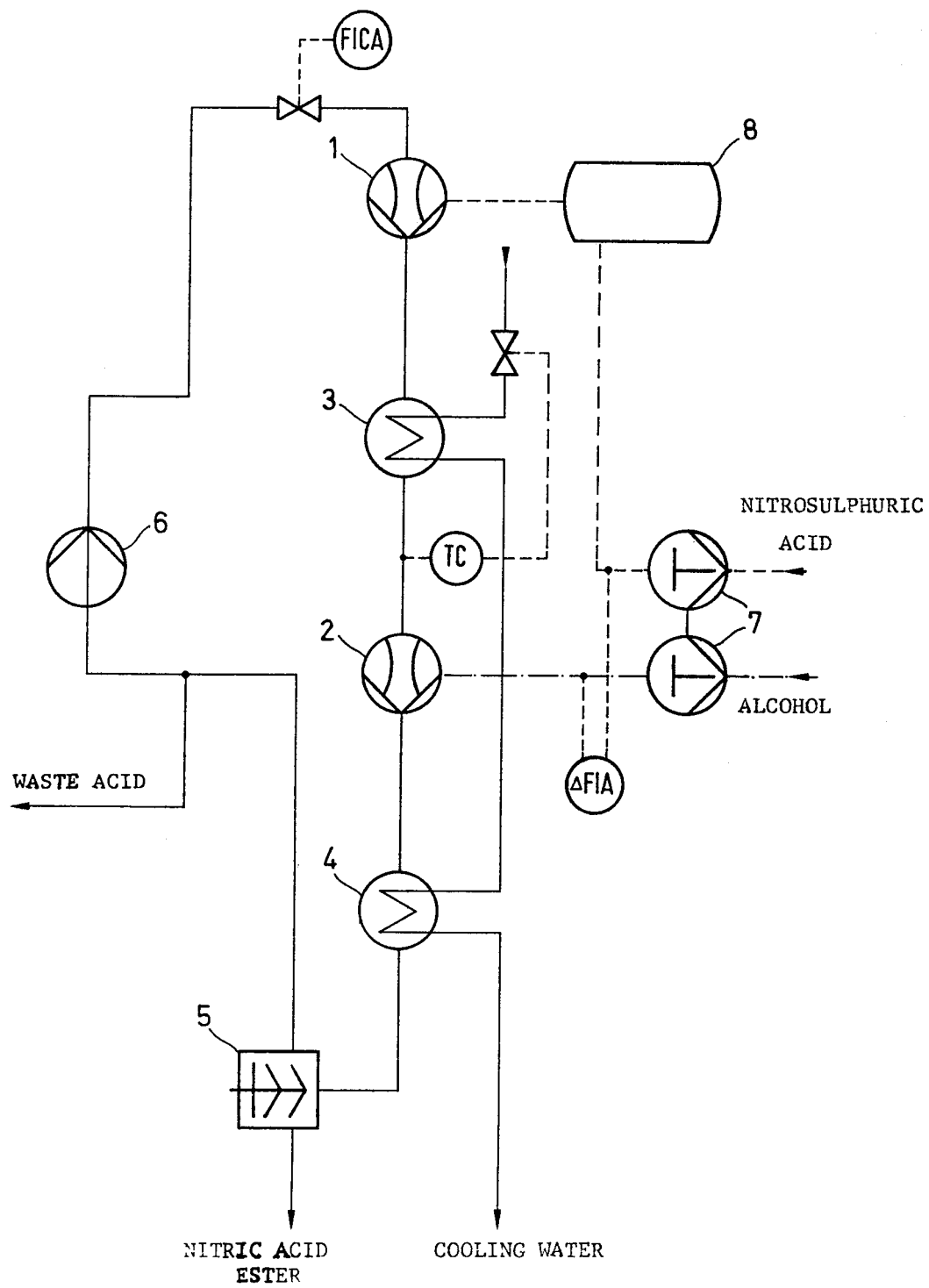

CONTINUOUS CLOSED LOOP NITRATION OF POLYHYDRIC ALCOHOLS

The invention relates to an improved process for the continuous manufacture of explosive liquid nitric acid esters from polyhydric alcohols, e.g. nitroglycerine, nitroglycol, dinitrodiglycol, etc., by a continuous circulation process. This process is considerably safer than the known batch processes or continuous processes, which require intermediate storage of large quantities of dangerous waste nitrating acid.

According to the heretofore conventional continuous processes for the manufacture of such nitric acid esters, the nitrating acid and the alcohol are fed into one apparatus, containing the waste acid, wherein the nitric acid ester obtained during the reaction is emulsified. The apparatus is equipped with a powerful mechanical stirring device as well as with a cooling device. A subsequent separator separates the nitric acid ester from the waste acid. This arrangement normally has a capacity of 500 to 2000 liters.

In the process of German Pat. No. 1,058,039 nitration takes place in an injector, the nitrating acid being fed to the injector under pressure, the alcohol being sucked in by means of the injector action.

Using this process the nitrating acid is produced in a separate vessel with the assistance of waste acid by the addition of fresh nitrosulphuric acid. For this purpose the intermediate storage of large volumes of waste acid is necessary so that this can be brought to the concentration of nitrating acid by addition of the nitrosulphuric acid.

For this method it is of course necessary that at least three spent acid reservoirs are available; in the first the spent acid is collected, in the second it is fortified and in the third conveyed out into the installation. For nitration an injector is used, which produces a gas dispersal in the liquid phase and an emulsification of the nitrating mixture by depression and simultaneous metering of an inert gas, e.g. nitrogen, carbon dioxide or air, and thus builds up a disperse system from gas, reaction products and waste acid. This gas dispersion can lead to accidents due to compression and decompression as in the case of known emulsion transports of nitroglycerines. In the further course of manufacture the heat of reaction in this process is discharged into a cooler and the nitric acid ester is separated from the spent acid in a subsequent separator.

The process of German Pat. No. 1,135,876 uses a device for the nitration of polyhydric alcohols in which the reaction is carried out by impinging the two reactants upon each other. The nitrating acid is manufactured in this process from the spent acid, conveyed via a pump receiver and a pump into a container, by adding nitrosulphuric acid. From this receiver the finished nitrosulphuric acid is passed back into the nitrating cycle. This arrangement requires a receiver and a storage vessel for waste acid which considerably increases the residence time of the circulating waste acid. The storage vessel must be equipped at least with a stirring member in order to produce a homogeneous nitrating acid from the waste acid and the fresh nitrosulphuric acid. The subsequent cooling of the nitrating mixture and the separation of the nitric acid ester is effected in conventional manner. Due to the buffering of the waste acid in the storage vessels even this process is not suitable for less stable waste acids such as are obtained during the manufacture of dinitrodiglycol. On the other hand it is generally desirable, in view of the numerous accidents even in the case of intermediate storage of stable waste acids, as occurs in the manufacture of nitroglycerine, to avoid intermediate storage.

These disadvantages are avoided in accordance with the present invention wherein the polyhydric alcohol is nitrated in a closed cycle from fortified waste acid. This cycle has a preferred residence time of less than about 15 minutes, preferably about 2 to 5 minutes, and the flow is turbulent with a Reynolds number of between about 2500 and 5000. Due to the high flow rate of the nitrating acid in this process and due to the small residence volumes, alcohols containing many hydroxy groups can also be nitrated using this process notwithstanding that the waste acid therefrom can lead to dangerous decomposition even after a short period of time.

Furthermore in this process no inert gases which can lead to dangerous compression are absorbed into the nitrating mixture stream. The ratio of alcohol to nitrosulphuric acid is kept automatically constant via a metering pump and the alcohol is fed into the circulating nitrating acid by means of an injection device operating under pressure.

The invention will be further described with reference to the accompanying drawing which is a flow sheet of the process.

Referring now more particularly to the drawing, 1 is a mixing injector through which waste acid is recycled, fresh nitrosulphuric acid coming into the injector and system from vessel 8. The mixture is cooled in cooler 3 with water which passes through a second cooler 4 before being discharged. Between the coolers 3 and 4 the mixture of waste acid and nitrosulphuric acid passes through an injector 2 through which polyhydric alcohol to be nitrated is supplied to the system by metering pump 7 which also governs the flow of fresh acid to vessel 8, maintaining the desired ratio with the assistance of a differential flow meter FIA.

The temperature between injector 2 and cooler 4 is kept at 20°–40° C., depending upon the type of alcohol to be nitrated. Cooler 4 brings the mass to room temperature. TC is a temperature control governing the rate of flow of cooling water.

In a centrifugal separator 5 liquid nitric acid ester product is removed from the system, the balance proceeding to a pump 6 for passage to a constant volume regulating valve FICA. A portion of the waste acid is withdrawn before the pump 6 to keep the volume in the system constant, irrespective of changes in the rates of addition of reactants at 7.

When it is desired to discontinue nitration or upon failure of current or other elements of the system, fresh nitrosulphuric acid is automatically supplied from pressurized buffer vessel 8 but without polyhydric alcohol while withdrawing unstable waste acid before pump 6.

The invention is further described in the following illustrative example:

EXAMPLE

Using an apparatus as shown in the drawing with a closed loop volume of 5 liters, the composition of the waste acid at injector 1 was:

| | |
|---|---|
| nitric acid | 12,5 parts by weight |
| sulphuric acid | 72,0 |

| | |
|---|---|
| water | 15,5 |

From vessel 8 nitrosulphuric acid of 42/55% concentration was supplied at the rate of 14 liters/hours and aqueous glycerine of 99% concentration was supplied to injector 2 at the rate of 3,45 liters/hours. Cooling water in Cooler 3 and 4 brought the temperature in each to 20° C. 12,5 parts by weights of trinitrate were withdrawn per minute in separator 5 along with 11 parts of nitric acid, 63 parts of sulphuric acid and 13,5 parts of water. 12,5 parts of nitric acid, 72 parts of sulphuric acid and 15,5 parts of water were withdrawn per minute before pump 6, keeping the volume substantially constant. The Reynolds number measured at injector 2 was 3500, liquid circulating through the system at the rate of 50 liters per hours with an average residence time of 3 minutes. After 3 hours of nitration the feed of glycerine was discontinued while being made up by additional nitrosulphuric acid so that in 4 minutes the system was substantially free of waste acid and glycerine trinitrate, comprising substantially pure nitrosulphuric acid.

It will be appreciated that the instant specification and examples are set forth by way of illustration and not limitation, and that various modifications and changes may be made without departing from the spirit and scope of the present invention.

What we claim is:

1. A process for the continuous manufacture of a nitric acid ester of a polyhydric alcohol by reacting the polyhydric alcohol with nitrating acid, comprising circulating a stream of waste nitrating acid through a closed loop, injecting nitrosulphuric acid into said circulating stream, cooling the stream downstream of the injection, feeding the alcohol via a mixer into the cooled stream, cooling the stream to remove heat produced by reaction, and separating nitrated polyhydric alcohol from the loop, along with sufficient waste acid to keep the volume in the loop substantially constant, circulation being carried out at a rate such that the average residence time of waste acid in the loop is less than about 15 minutes.

2. A process according to claim 1, wherein the average residence time of the waste acid is from about 2 to 5 minutes.

3. A process according to claim 1, wherein circulation is effected with a Reynolds number from about 2500 to 5000.

4. A process according to claim 1, wherein separation of the polyhydric alcohol nitrated from the nitrating mixture is effected in a centrifugal separator.

5. A process according to claim 1, wherein feed of the nitrosulphuric acid is effected from a pressurized buffer vessel, and upon discontinuance of nitration nitrosulphuric acid from said vessel is supplied to said loop so as substantially to displace the waste acid from the loop.

* * * * *